US010580181B2

(12) United States Patent
Shen

(10) Patent No.: US 10,580,181 B2
(45) Date of Patent: Mar. 3, 2020

(54) METHOD AND SYSTEM FOR GENERATING COLOR MEDICAL IMAGE BASED ON COMBINED COLOR TABLE

(71) Applicant: SHANGHAI UNITED IMAGING HEALTHCARE CO., LTD., Shanghai (CN)

(72) Inventor: Jianhua Shen, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 236 days.

(21) Appl. No.: 15/691,815

(22) Filed: Aug. 31, 2017

(65) Prior Publication Data
US 2018/0260989 A1 Sep. 13, 2018

Related U.S. Application Data

(63) Continuation of application No. PCT/CN2017/075892, filed on Mar. 7, 2017.

(51) Int. Cl.
*G06T 11/60* (2006.01)
*G06T 7/00* (2017.01)
(Continued)

(52) U.S. Cl.
CPC ............ *G06T 11/60* (2013.01); *G06F 3/0487* (2013.01); *G06F 3/14* (2013.01); *G06T 7/0012* (2013.01); *G06T 7/11* (2017.01); *G06T 11/00* (2013.01); *G06T 11/001* (2013.01); *G09G 5/06* (2013.01); *G06T 2207/10024* (2013.01); *G06T 2207/10028* (2013.01); *G06T 2207/10081* (2013.01); *G06T 2207/10088* (2013.01);
(Continued)

(58) Field of Classification Search
None
See application file for complete search history.

(56) References Cited

U.S. PATENT DOCUMENTS

| 6,549,645 B1 | 4/2003 | Oikawa et al. |
| 7,561,728 B2 | 7/2009 | Abufadel et al. |

(Continued)

FOREIGN PATENT DOCUMENTS

| CN | 101336831 A | 1/2009 |
| CN | 103300856 A | 9/2013 |
| CN | 104167010 A | 11/2014 |

OTHER PUBLICATIONS

Alexander Wong et al., Intervertebral Disc Segmentation and Volumetric Reconstruction From Peripheral Quantitative Computed Tomography Imaging, IEEE Transactions on Biomedical Engineering, vol. 56, No. 11, Nov. 2009(2748-2751).

(Continued)

*Primary Examiner* — Tahmina N Ansari
(74) *Attorney, Agent, or Firm* — Metis IP LLC

(57) ABSTRACT

The present disclosure discloses a method for generating color medical image. The method for generating color medical image comprising: acquiring medical image data, segmenting at least one tissue in the medical image data, determining a combined color table from a combined color table database based on the at least one tissue; and generating a color medical image based on the combined color table. In some embodiments, the combined color table comprises data of color schemes for the segmented tissues.

19 Claims, 11 Drawing Sheets

(51) Int. Cl.
  *G09G 5/06* (2006.01)
  *G06T 11/00* (2006.01)
  *G06T 7/11* (2017.01)
  *G06F 3/0487* (2013.01)
  *G06F 3/14* (2006.01)

(52) U.S. Cl.
  CPC .............. *G06T 2207/10104* (2013.01); *G06T 2207/10108* (2013.01); *G06T 2207/10132* (2013.01); *G06T 2207/30024* (2013.01); *G06T 2211/404* (2013.01); *G06T 2211/412* (2013.01); *G09G 2380/08* (2013.01)

(56) References Cited

U.S. PATENT DOCUMENTS

| | | | |
|---|---|---|---|
| 9,445,744 B2 | 9/2016 | Liu et al. | |
| 2008/0260227 A1* | 10/2008 | Hayashi | A61B 8/06 382/131 |
| 2009/0174729 A1 | 7/2009 | Matsumoto | |
| 2010/0111396 A1* | 5/2010 | Boucheron | G06K 9/0014 382/133 |
| 2012/0095320 A1 | 4/2012 | Miyazaki | |
| 2016/0278743 A1 | 9/2016 | Kawashima | |
| 2017/0064319 A1* | 3/2017 | Fram | G16H 30/20 |
| 2018/0260989 A1* | 9/2018 | Shen | G06T 7/11 |
| 2018/0322635 A1* | 11/2018 | Guo | G06T 7/149 |

OTHER PUBLICATIONS

Claudia Chevrefils et al., Texture Analysis for Automatic Segmentation of Intervertebral Disks of Scoliotic Spines From MR Images, IEEE Transactions on Information Tech in Biomedicine, vol. 13, No. 4, Jul. 2009 (608-620).

Zhao, Guofeng, Multislice spiral CT multiplanar reconstruction (MPR) in the diagnosis of lumbar disc herniation, China Practical Medicine, Jun. 2008, vol. 3, No. 16. (83-84).

* cited by examiner

METHOD AND SYSTEM FOR GENERATING COLOR MEDICAL IMAGE BASED ON COMBINED COLOR TABLE

CROSS-REFERENCE TO RELATED APPLICATIONS

This application claims priority of PCT Application No. PCT/CN2017/075892, filed on Mar. 7, 2017, the contents of which are incorporated herein by reference.

TECHNICAL FIELD

The present disclosure generally relates to methods and systems for generating a color medical image, and more particular relates to methods and systems for generating a color medical image based on a combined color table.

BACKGROUND

With the wide use of the medical imaging in the medical field, people begin to make effort to improve the quality of the medical image and enhance the identification of the medical image display. In the medical imaging field, there is a number of image information, including a XR image, a CT image, an MR image, an ultrasound image, and the like. Most of the image data may represent signal strength, for example, CT value may represent the tissue's absorbency of X-ray and reflect the density of tissue. Most of the signals are one-dimensional signals which is called drawing images in the form of the image. Generally human eyes have poor ability to distinguish black and white gray scale level, and most may only distinguish twenty grayscale levels and be not sensitive to the grayscale changes. However, the human eyes can simultaneously distinguish thousands of color images having different brightness, hues and saturation. Therefore, people often convert a grayscale image into a color image to display. Slight grayscale difference which can be not distinguished by the human eyes may be displayed as significant color difference, thereby improving the authenticity of the images, the medical staff may obtain more image information from the image, and contribute to the diagnosis of diseases. At present, color display technique used in the medical image is color table (pseudo-color table), that represents different gray levels by different colors and transparencies, thereby achieving the purpose of that medical image may be displayed by color means. With the development of the medical application, one medical image may commonly contain a plurality of tissues, whereas the medical application need to simultaneously display the tissues and distinguish the tissues in the medical application. This requires a plurality of color tables to separate different tissue regions on basis of image segmentation, achieve the purpose of displaying the tissues. Although the plurality of tissues may be simultaneously displayed using the plurality of color tables, switching the tissues display and revising configuration information of a certain color table is cumbersome. It is necessary for the medical personnel to perform many steps to realize, this caused the operation more complex and time-consuming.

SUMMARY

In accordance with some embodiments of the disclosed subject matter, a method implemented on at least one processor and a storage medium for generating color medical image is provided. The method for generating color medical image comprises: acquiring medical image data; segmenting at least one tissue from the medical image data; determining a combined color table from a combined color table database based on the at least one tissue; and generating a color medical image including the at least one tissue based on the combined color table, wherein the combined color table comprises data of color schemes for the segmented at least one tissue.

Another aspect of the present disclosure relates to a non-transitory computer readable medium. The non-transitory computer readable medium storing executable instructions that, when executed by at least one processor, cause the at least one processor to effectuate a method. The method comprises: acquiring medical image data; segmenting at least one tissue from the medical image data; determining a combined color table from a combined color table database based on the at least one tissue; and generating a color medical image including the at least one tissue based on the combined color table, wherein the combined color table comprises data of color schemes for the segmented at least one tissue.

Another aspect of the present disclosure relates to a color image generating system. The color image generating system comprising: at least one processor; and executable instruction, the instructions, when executed by at least one processor, cause the at least one processor to implement a color image generating method. The color image generating method comprises: acquiring medical image data; segmenting at least one tissue from the medical image data; determining a combined color table from a combined color table database based on the at least one tissue; and generating a color medical image including the at least one tissue based on the combined color table, wherein the combined color table comprises data of color schemes for the segmented at least one tissue.

In some embodiments, the method for generating color medical image, further comprises displaying the color medical image including the at least one tissue to a user.

In some embodiments, determining a combined color table from a combined color table database based on the at least one tissue comprises: determining at least one type of the at least one tissue; retrieving at least one combined color table related to the at least one type of the at least one tissue from the combined color table database; displaying the at least one combined color table to a user; receiving an instruction for selecting the combined color table from the at least one combined color table; and determining the combined color table.

In some embodiments, the method for generating color medical image, further comprises a generating method for generating the combined color tables in the combined color table database, the generating method comprises: determining a tissue number of the at least one tissue; determining a color table for each tissue of the at least one tissue; determining another color table based on the determined color table for the first tissue of the at least one tissue until color tables for all of the at least one tissue are determined; and combining the color tables for all of the at least one tissue as a combined color table.

In some embodiments, the method further comprises a revising method for revising the combined color table in the combined color table database, the revising method comprising: acquiring the combined color table; determining data that needs to be revised in the combined color table; determining a new combined color table by revising the data; and storing the new combined color table in the combined color table database.

In some embodiments, the medical image data comprises at least one of a 2D image data, a 3D image data, and a dynamic image data.

In some embodiments, the segmenting at least one tissue from the medical image data comprises: segmenting different tissues from the medical image data, and segmenting different portions from a tissue of the at least one tissue.

In some embodiments, the color scheme comprises at least information of number, name, label, color, transparency, and whether to hide.

In some embodiments, the combined color table comprises: a subset of the medical image data corresponding to a plurality of tissues; and color tables corresponding to the plurality of tissue, respectively, each of the plurality of color tables comprising a window width and a window level with respect to the each of the plurality of tissues and a color effect corresponding to a gray value determined by the window width and window level.

In some embodiments, the determining at least one type of the at least one tissue comprises: determining at least one type feature of the at least one tissue, the at least one type feature of the at least one tissue comprising at least one type of the at least one tissue, a number of different types of the at least one tissue and morphology of the at least one tissue.

In some embodiments, an instruction of determining the combined color table from the at least one combined color table is transmitted by a user via an interactive device, wherein the interactive device displays the at least one combined color table in a displaying format comprising list, diagram, and preview image generated by applying the combined color table to the medical image including the at least one tissue.

In some embodiments, the retrieving at least one combined color table related to the at least one type of the at least one tissue is based on at least one type feature of the at least one tissue.

In some embodiments, the combined color table further comprises one or more options as to whether to display or hide each of the at least one tissue.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings.

DETAILED DESCRIPTION

Figure 1:
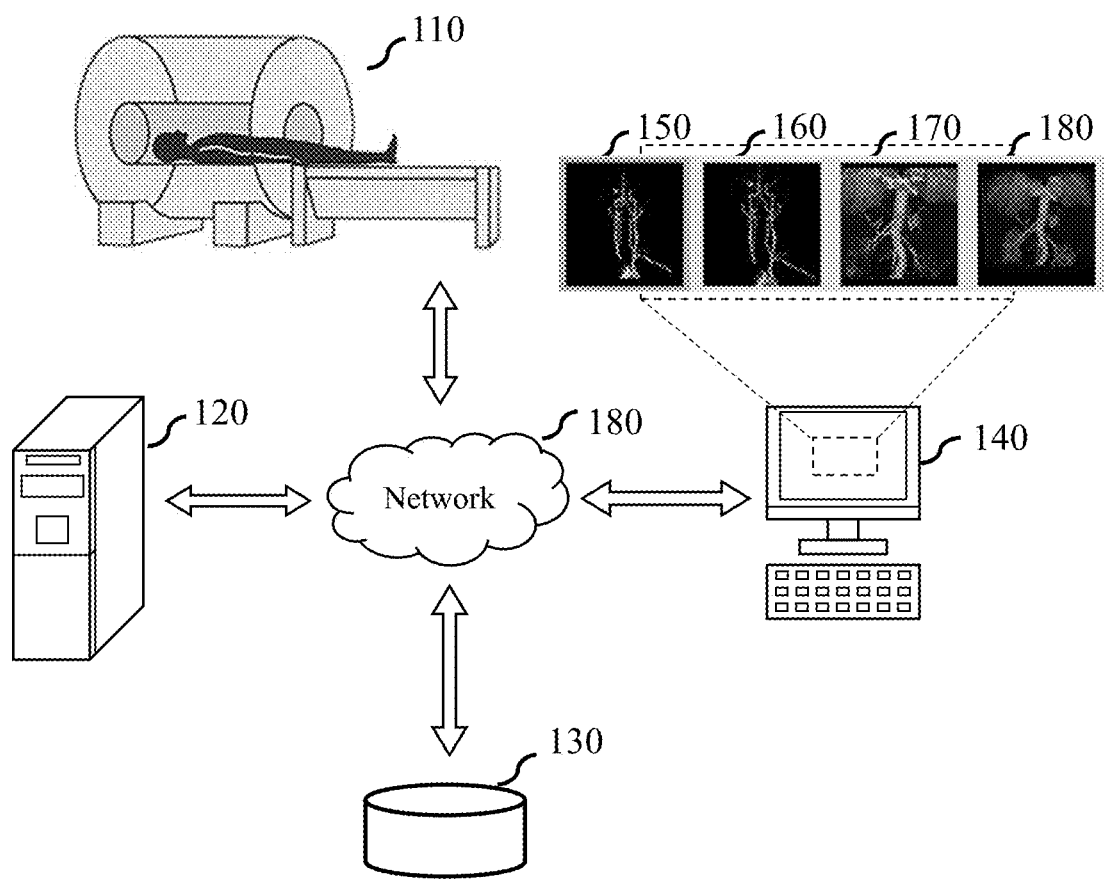
FIG. 1 is a schematic diagram of a color medical image generating system according to some embodiments of the present disclosure.

In order to illustrate the technical solutions related to the embodiments of the present disclosure, brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation As used in the disclosure and the appended claims, the singular forms "a," "an," and "the" include plural referents unless the content clearly dictates otherwise. It will be further understood that the terms "comprises," "comprising," "includes," and/or "including" when used in the disclosure, specify the presence of stated steps and elements, but do not preclude the presence or addition of one or more other steps and elements.

Some modules of the system may be referred to in various ways according to some embodiments of the present disclosure, however, any number of different modules may be used and operated in a client terminal and/or a server. These modules are intended to be illustrative, not intended to limit the scope of the present disclosure. Different modules may be used in different aspects of the system and method.

According to some embodiments of the present disclosure, flow charts are used to illustrate the operations performed by the system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

In the process of image processing, "image segmentation", "image extraction", and "image classification" may each means selecting an image that satisfies a specific condition from a large region and may be used interchangeably. According to some embodiments of the present disclosure, an imaging system may include one or more formats. The formats may include but are not limited to digital subtraction angiography (DSA), magnetic resonance imaging (MRI), magnetic resonance angiography (MRA), computed tomography (CT), computed tomography angiography (CTA), ultrasonic scanning (US), positron emission tomography (PET), single photon mission computed tomography (SPECT), SPECT-MR, CT-PET, CE-SPECT, DSA-MR, PET-MR, PET-US, SPECT-US, TMS-MR, US-CT, US-MR, X-ray-CT, X-ray-PET, X-ray-US, video-CT, video-US, or the like, or any combination thereof. In some embodiments, a subject of image scanning may include an organ, a body, an object, an injured section, a tumor, or the like, or any combination thereof. In some embodiments, a subject of image scanning may include a brain, a thorax, an abdomen, an organ, a bone, a vessel, or the like, or any combination thereof. In some embodiments, a subject of image scanning may include blood vessels of one or more tissues. In some embodiments, the image may include a 2-dimensional image and/or a 3-diemnsional image. A smallest divisible element of the 2-dimensional image may be a pixel. A smallest divisible element of the 3-dimensional image may be a voxel. The 3-dimensional image may include a series of 2-dimensional slices and/or 2-dimensional layers.

A process of tissue segmentation may be performed based on features corresponding to the pixels (or voxels) of an image. In some embodiments, the features corresponding to the pixels (or voxels) may include texture, grayscale, average grayscale, signal strength, color saturation, contrast, brightness, or the like, or any combination thereof. In some embodiments, a spatial position feature corresponding to the pixels (or voxels) may be used in the process of image segmentation.

It should be noted that the above description of the image processing system is merely provided for the purposes of illustration, and not intended to limit the scope of the present disclosure. It should be understood that, for persons having ordinary skills in the art, within the scope of the present disclosure, various modules may be combined, or subsystem may be connect to other modules, various modifications and changes may be performed in the form and details of the disclosed methods and systems described above.

FIG. 1 is a schematic diagram of a color medical image generating system according to some embodiments of the present disclosure. The color medical image generating system 100 may include a data collection device 110, a processing device 120, a memory 130, and an interactive device 140. The data collection device 110, the processing device 120, the memory 130 and the interactive device 140 may communicate with each other via a network 180.

The data collection device 110 may be configured to collect data. The data may include image data, object feature data, and the like. In some embodiments, the data collection device 110 may include an imaging device. The imaging device may collect the image data. The imaging device may be a magnetic resonance imager (MRI), a computed tomography scanner (CT), a positron emission topography (PET), a b-scan ultrasonography, a diasonography diagnostic device, a thermal texture mapping (TTM), a medical electronic endoscope (MEE), and the like, and one or more combinations thereof. The image data may include an image or data of a blood vessel, a tissue or an organ of an object. In some embodiments, an object feature collection device may be integrated in the imaging device so that the image data and the object's features may be collected simultaneously. In some embodiments, the data collection device 110 may send the collected data to the processing device 120, the memory 130 and/or the interactive device 140, and the like via the network 180.

The processing device 120 may process data. The data may be collected by the data collection device 110. The data may also be obtained from the storage device 130, the communication device 140 (e.g., input data of a user), or from a cloud or an external device via the network 180. In some embodiments, the data may include image data, object's features data, user input, etc. The processing of the data may include selecting a region of interest from the image data. The region of interest may be selected solely by the processing device 120, or selected based on user input. In some embodiments, the region of interest may include a blood vessel, a tissue, an organ, etc. For example, the region of interest may be an artery, such as a coronary artery, an abdominal artery, a brain artery, a lower extremity artery, etc. The processing device 120 may further segment the region of interest. The technique of image segmentation may include a technique based on edges (e.g., a Perwitt operator, a Sobel operator, a gradient operator, a Kirch operator, etc.), a technique based on regions (e.g., a region growing technique, a threshold technique, a clustering technique, etc.), or other techniques based on fuzzy sets, a neural network, etc.

In some embodiments, the processing device 120 may segment difference tissues. For example, the grayscale image of the head region may be segmented into a head vessel, a head thin vessel, a head bone, head skin, etc. The tissue segmentation may be performed based on a method of a user identification, or an interactive segmentation method, and may be also performed based on an algorithm of automatically segmenting the tissue, such as a region growing algorithm, an algorithm based on the grayscale, a level set, a neural network, a clustering method, a graph cut, a deformable model, an atlas method, and the like.

In some embodiments, the processing device 120 may convert a grayscale image into a color medical image according to a combined color table. The combined color table may include: the plurality of tissues, wherein the tissues represent partial regions or a subset of medical image data; a color table corresponding to each tissue, wherein the color table may include window width and window level of the tissue and a color effect corresponding to a gray value determined by the window width and window level; and information for determining whether to hide the tissues and transparency information of the tissues. For example, a head grayscale image is processed by the different color schemes, and the processing result may include a color medical image about the head vessel 150, a color medical image about the head thin vessel 160, a color medical image about the head vessel and a skull 170, a color medical image about the head thin vessel and the skull 180, and one or more combinations thereof.

In some embodiments, the processing device 120 may edit a tissue control module corresponding to the combined color table, such as tissue display control, the color of each tissue, color table control, the transparency, illumination parameter, etc. In some embodiments, the processing device 120 may revise a transparency parameter of a certain tissue in the determined combined color table. In some embodiments, the processing device 120 may revise color parameters of certain tissues in the determined combined color table.

In some embodiments, the processing device 120 may perform noise reduction or smoothing processing on the acquired data or the processing result. In some embodiments, the acquired data or the processing result may be sent to and store into the memory 130, or may be sent to the interactive device 140 to display, by the processing device 120. The processing result may be an intermediate result generated during the processing process, for example a tissue segmentation result, and may also be a final processing result, such as a final obtained color medical image. In some embodiments, the processing device 120 may be one or more processing elements or devices, such as a central processing unit (CPU), a graphic processing unit (GPU), a digital signal processor (DSP), a system-on-a-chip (SoC), a microcontroller (MCU), etc. In some embodiments, the processing device 120 may also be a special designed processing element or device with special function. The processing device 120 may be native, or be remote in relation to the data collection device 110.

The memory 130 may store data or information. The data or information may include the data acquired by the data collection device 110, a processing result or a control instruction generated by the processing device 120, and the user input data received by the interactive device 140, and the like. The memory 130 may be one or more storage mediums for reading from and writing, including a static random access memory (SRAM), a random access memory (RAM), a read only memory (ROM), a hard disk, a flash memory, and the like. In some embodiments, the memory 130 may also be a remote memory, such as a cloud drive, and the like.

The interactive 140 may be configured to receive, send, and/or display data or information. The received data or information may include the data obtained by the data collection device 110, the processing results generated by the processing device 120, the data stored by the storage device 130, etc. For example, the data or information displayed by the communication device 140 may include an actual image 150 of a cardiovascular obtained by the data collection device 110, a cardiovascular model 160 reconstructed by the processing device 120 based on the actual image 150, a coronary artery model extracted from the cardiovascular model 160 by the processing device 120, etc. The formats of display may include but is not limited to a 2-dimensional or 3-dimensional medical image, a geometric model and its grid processed result, a vector diagram (e.g., a velocity vector), a contour map, a filled contour map (cloud chart), an XY scatter plot, a particle trajectory map, a simulated flow effect, or the like, or any combination thereof. As another example, the data or information sent by the communication device 140 may include input information of a user. The communication device 140 may receive one or more operating parameters of the processing device 120 input by the user, and send the operating parameters to the processing device 120. In some embodiments, the communication device 140 may include a user interface. The user may provide a user input to the communication device 140 by specific interactive apparatuses such as a mouse, a keyboard, a touchpad, a microphone, etc.

In some embodiments, the communication device 140 may be a device with displaying function, such as a screen. In some embodiments, the communication device 140 may have some or all functions of the processing device 120. For example, the communication device 140 may implement operations (e.g., smoothing, denoising, changing colors, etc.) to the results generated by the processing device 120. Merely by way of example, the operation of changing colors may include transferring a grayscale image to a color image, or transferring a color image to a grayscale image. In some embodiments, the communication device 140 and the processing device 120 may be an integrated device. The integrated device may implement functions of both the processing device 120 and the communication device 140. In some embodiments, the communication device 140 may include a desktop computer, a server, a mobile device, etc. The mobile device may include a laptop computer, a tablet computer, an iPad, a built-in device of a vehicle (e.g., a motor vehicle, a ship, and an airplane), a wearable device, etc. In some embodiments, the communication device 140 may include or is connected to a display apparatus, a printer, a fax machine, etc.

The network 180 may be used for internal communication of the color medical image generating system 100. The network 180 may also be configured to receive information from or send information to the external devices outside the system 100. In some embodiments, the data collection device 110, the processing device 120, and the communication device 140 may be connected to the network 180 via a wired connection, a wireless connection, or a combination thereof. The network 180 may be a single network or a combination of networks. In some embodiments, the network 180 may include but is not limited to a local area network (LAN), a wide area network (WAN), a public network, a proprietary network, a wireless local area network (WLAN), a virtual network, an urban metropolitan area network, a public switched telephone network (PSTN), or the like, or any combination thereof. In some embodiments, the network 180 may include multiple network access points, such as a wired or wireless access point, a base station or network switched point, etc. Through these access points, any data source may be connected to the network 180 and transmit information via the network 180.

Figure 2:
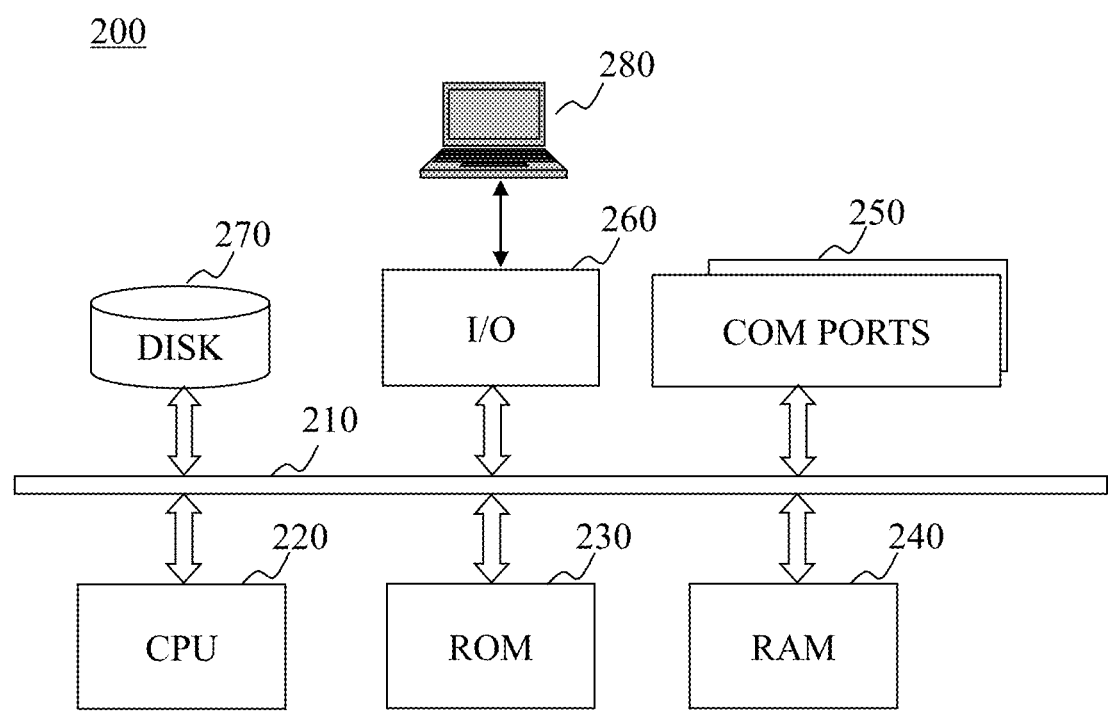
FIG. 2 is schematic diagram of a computing device according to some embodiments of the present disclosure.

FIG. 2 is schematic diagram of a computing device according to some embodiments of the present disclosure. The computing device 200 may implement a specific system of the present disclosure. The specific system of the present disclosure may use a functional diagram to describe a hardware platform including a user interface. The computing device 200 may configured to implement one or more components, modules, units, sub-units (e.g., the processing device, the interactive device, etc.) of the color medical image generating system 100. The one or more components, modules, units, sub-units (e.g., the processing device, the interactive device, etc.) of the color medical image generating system 100 may be implemented by the computing device 200 by a hardware device, a software program, a firmware, or any combination thereof of the computing device 200. The computing device 200 may be a general purpose computing device, or a specific purpose computing device. The computing devices may be configured to implement the specific system of the present disclosure. For brevity, the FIG. 2 illustrates only one computing device. According to some embodiments, functions of processing and pushing information may be processing loads of a decentralized system implemented on a set of similar platforms in a distributed manner.

As showed in FIG. 2, the computing device 200 may include an internal communication bus 210, a processor 220, a read-only memory (ROM) 240, a random-access memory (RAM) 240, a communication port 250, an input/output component 260, a hard disk 270, a user interface 280, etc. The internal communication bus 210 may be configured to implement data communications between components of the computing device 200. The processor 220 may implement program instructions to complete one or more functions, components, modules, units, sub-units of the color medical image generating system 100 disclosure in the present disclosure. The processor 220 may include one or more processors. The commination port 250 may be configured to implement data communications (e.g., via the network 180) between the computing device 200 and other parts (e.g., the data connection device 110) of the color medical image generating system 100. The computing device 200 may include different forms of program storage unit and data storage unit, such as a hard disk 270, a read-only memory (ROM) 230, a random access memory (RAM) 240, and various data files used by a computing device for processing or communication, a possible program instruction implemented by the processor 220. The input/output component 260 may support inputting/outputting data stream between the computing device 200 and other components (e.g., the user interface 280), and/or other components of the color medical image generating system 100. The computing device 200 may send and receive information and data by the communication port 250 via the network 180.

Figure 3:
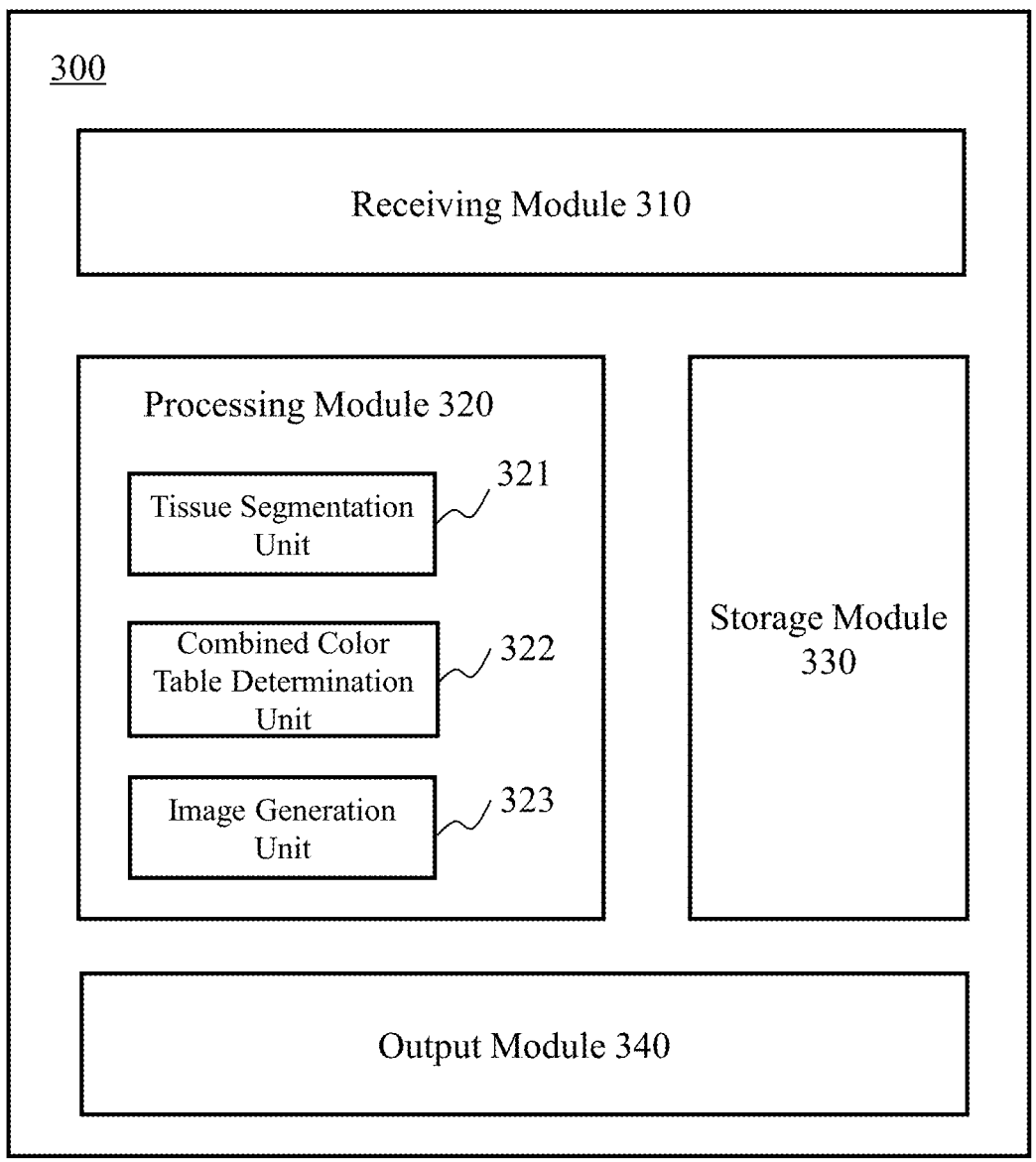
FIG. 3 is a schematic diagram of the color medical image generating system according to some embodiments of the present disclosure.

FIG. 3 is a schematic diagram of the color medical image generating system according to some embodiments of the present disclosure. The color medical image generating system 300 may include a receiving module 310, a processing module 320, a storage module 330 and an output module 340. The processing module 320 may also include a tissue segmentation unit 321, a combined color table determination unit 322 and an image generation unit 323. The modules may be directly (and/or indirectly) connected to each other.

The receiving module 310 may receive the medical image. The medical image may include a XR image, a CT image, a MR image, an ultrasound image, etc. The medical image may reflect information of a part of the tissues of human body or animals and plants. In some embodiments, the medical image is one or a set of two-dimensional images, for example, a black and white X-ray film, CT images of different faults, etc. The two-dimensional medical image may consist of certain pixels. In some embodiments, the medical image may be a three-dimensional space model, for example, an organ three-dimensional model rebuilt based on the CT images of different faults, or a three-dimensional space model output by a device with a three-dimensional angiography ability. The three-dimensional medical image may consist of certain voxels. In some embodiments, the medical image maybe a dynamic image during a period of time, for example, a video that reflects the changes of a heart and surrounding tissues within one cardiac cycle. The medical image may be obtained from the imaging device 110, the storage module 330, or from the user input through the interactive device. In some embodiments, the pixels or voxels consisting of the medical image are black and white pixels or voxels. The grayscale value of the pixel or voxel may accordingly change with the different forms of the imaging tissue organ to present the black and white tissue organ image. The pixel or voxel and the corresponding grayscale value may be stored in the storage module 330 in the form of a list. In some embodiments, the pixels or voxels belonging to a certain tissue organ may correspond to a part of the grayscale values. For example, the bone, the muscle and the skin tissue may exist simultaneously in some medical images. Each tissue may respectively correspond to a value range of a certain grayscale value. For example, the grayscale value of the bone is higher, the grayscale value of the muscle is the secondary, the grayscale value of the skin is the smallest, and the like.

The processing module 320 may process the medical images received by the receiving module 310. The processing may include: segmenting different tissues or segmenting different portions of a tissue, determining a color scheme for the segmented tissues, and generating a color medical image based on the determined color scheme. The processing may be separately implemented by the tissue segmentation unit 321, the combined color table determination unit 322, and the image generation unit 323.

The tissue segmentation unit 321 may segment different tissues or segmenting different portions of a tissue in the received medical image. The segmentation may be performed automatically, semi-automatically or manually. The different tissues may be different organs included in the medical image, such as bone, skin, visceral organ, and the like. The different portions of a tissue may be the parts in the different positions in a certain tissue organ, such as a left lung lobe and a right lung lobe of the human body, etc. In some embodiments, the segmentation may be used to classify the pixels or voxels corresponding to different tissues. For example, in the medical image including bone, muscle and skin, the pixels or voxels corresponding to the bone may be divided into a first class, the pixels or voxels corresponding to the muscle may be divided into a second class, and the pixels or voxels corresponding to the skin may be divided into a third class. The classification information of the pixel or voxel may be stored into the storage module 330.

The combined color table determination unit 322 may determine a combined color table for generating a color medical image assist. In some embodiments, the combined color table may consist of a series of color tables. The color table may be a color table (pseudo-color table) that is currently used in color display technology in the medical image. The color table may display different colors and/or transparencies for the different grayscales or different grayscale intervals. For example, the higher grayscale values may correspond to colors with longer wavelength, or a certain grayscale interval corresponds to a same color. In some embodiments, the color table may also correspond to a certain type of pixels or voxels. For example, the same type of pixels or voxels may correspond to the same color. In some embodiments, contents of the color table may include number, name, label, color, transparency, or whether to hide. The information whether to hide may be judgment information about yes or no. For example, when information whether to hide is yes, the type of tissues may be hidden from the final generated color medical image. In some embodiments, the analysis and the storage of the combined color table may be performed by extensible markup language Xml technology.

In some embodiments, the combined color table may be a set of at least two color tables. For example, a certain combined color table may include the color table of bone and skin. In the color medical image generated based on the combined color table, the bone may be generated based on the information of the bone in the combined color table, and the skin may be generated based on the information of the skin in the combined color table. In some embodiments, the information of different types of tissues in the combined color table may be interrelated mutually. For example, in the combined color table including the bone and the skin, there may be significant difference between the color of the bone information and the color of the skin information, thereby facilitating the human eyes to distinguish when the color medical image is generated. As another example, a tissue A may be completely surrounded by a tissue B when the three-dimensional color medical image is generated. In the corresponding combined color table, the user may choose to hide the tissue B, thereby facilitating display of the tissue A in the three-dimensional color medical image when you need to observe the tissue A.

In some embodiments, the combined color table may be stored into a combined color table database. For example, the analysis and storage of the combined color table may be implemented by the Xml technology. The user may invoke the required combined color table from the combined color table database according to the actual demands. The combined color table determination unit 322 may determine different combined color tables segmented based on the different tissues, from the combined color table according to the user instruction, and perform the subsequent operation for generating the color medical image. In some embodiments, the management of the combined color table may be implemented by Model-view-controller (MVC). That is, the contents of the combined color table are taken as a model, and the displayed contents are taken as a view. In this way, the plurality of tissues segmentation selected by the users may be realized, the related combined color table modules may be automatically acquired from the combined color table database, and the color medical image including the plurality of tissues segmentations may be generated in one step.

The image generation unit 323 may generate color medical image based on the combined color table determined by the combined color table determination unit 322. The generating method may be a rendering technology based one color table, such as a volume rendering technology based on the light radiation which is applied in a virtual reality (VR) and a maximum intensity projection (MIP) of the medical image. The volume rendering technology based on the light radiation may implement the simulation of the ray-casting by the Shader technology of OpenGL. In some embodiments, the rendering technology may be a rendering technology based on multithreaded CPU or GPU.

The storage module 330 may store data or information. The stored data or information may be in various forms, such as, value, signal, image, the related information of a target object, command, algorithm, program, and the like, or a combination thereof. In some embodiments, the stored data may be the black and white medical image, the color medical image, the tissue color table, the combined color table, or the program and/or algorithm applied in the image processing.

The output module 340 may output the generated color medical image. For example, the output module 340 may send the color medical image to the memory 130 to store, or send the color medical image to the interactive device 140 to display, or present the color medical image to the client in other ways (such as image, sound, etc.). The displayed contents may be generated middle results, such as a model of the region of interest, or the generated final results, such as tissue segmentation during generation of a color medical image.

It should be noted that the above description of the color medical image generating system 300 is merely provided for the purposes of illustration, and not intended to limit the scope of the present disclosure. It should be understood that, for persons having ordinary skills in the art, within the scope of the present disclosure, various modules may be combined, or subsystem may be connect to other modules, various modifications and changes may be performed in the form and details of the disclosed methods and systems described above.

Figure 4:
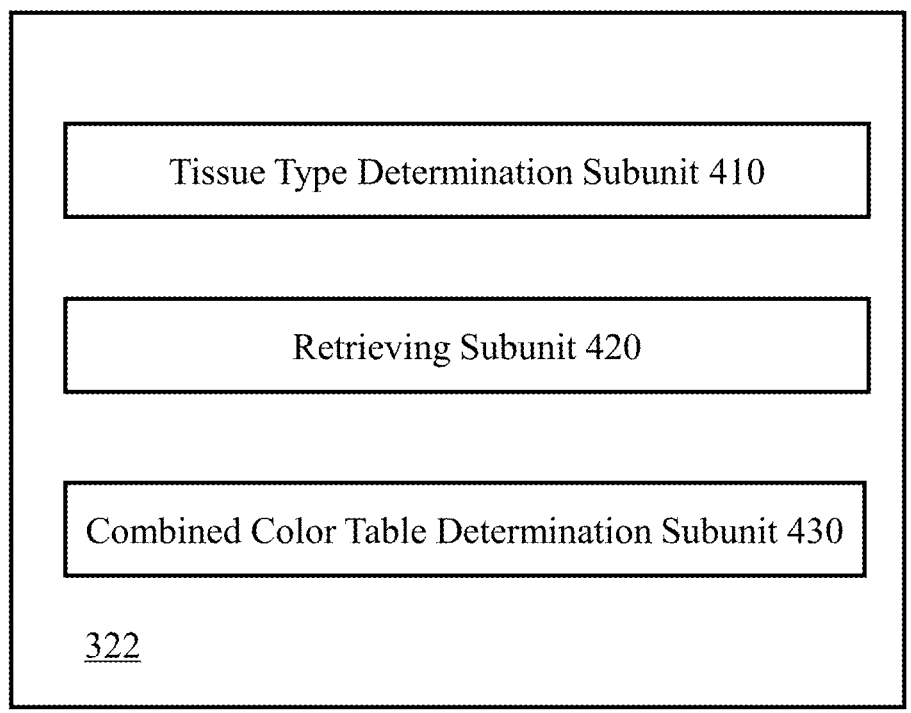
FIG. 4 is a schematic diagram of a combined color table determination unit according to some embodiments of the present disclosure.

FIG. 4 is a schematic diagram of a combined color table determination unit according to some embodiments of the present disclosure. The combined color table determination unit 322 may include a tissue type determination subunit 410, a retrieving subunit 420 and a combined color table determination subunit 430. The modules may be directly (and/or indirectly) connected with each other.

The tissue type determination subunit 410 may determine the type features of the tissues included in the received medical image. The type features may include types of the tissues, amount of different tissues, and morphology of the tissues. In some embodiments, the number of types of the tissues may be determined by the tissue type determination subunit 410. For example, a certain medical image includes bone, skin and muscle, and three types of the tissues may be determined. In some embodiments, the amount of a certain type of the tissues may be determined. For example, five vertebras are included in a certain medical image, and the five vertebras may be determined. In some embodiments, the morphology of a certain tissue may also be determined. For example, a cardiac morphology of some cardiac patient is different from the cardiac morphology of ordinary person since the cardiac patient has some disease, the morphological feature may be determined. The series of type features may be used as the image feature of the received medical image, and provided reference for generating the subsequent color image.

The retrieving subunit 420 may retrieve in the combined color table database based on the type features determined by the tissue type determination subunit 410. The combined color table database may be stored in either the storage module 330 or a certain cloud server, and be accessed by the network 180. In some embodiments, the retrieving may be performed hierarchically. For example, the retrieving may be firstly performed by the type and number of the tissues. For example, three types of the tissues bone, skin and muscle are included in a medical image, and the first retrieving may screen out a combined color table, whose information about the types of the tissues consists of bone, skin and muscle. The further retrieving may be performed by the specific number of the certain tissues. For example, in the medical image including five vertebras, the combined color table including five vertebras may be further screened from the first retrieving result. The more retrieving may be performed by the morphology of certain tissues. For example, in the medical image including two lung lobes, the combined color table including the information about two lung lobes may be screened from the first or further retrieving result. After at least one layer of retrieval, there may be a number of associated combined color tables that are screened as retrieving results.

The combined color table determination subunit 430 may determine a series of retrieving results screened by the retrieving subunit 420. In some embodiments, the series of retrieving results may be displayed on the interactive device 140. The displaying mode may include a list, a schematic, and a preview image of the color medical image generated based on the combined color table. A user may perform the determination operation using the interactive device 140, and the combined color table may be determined by the combined color table determination subunit 430.

It should be noted that the above description of combined color table selection unit 322 is merely provided for the purposes of illustration, and not intended to limit the scope of the present disclosure. It should be understood that, for persons having ordinary skills in the art, within the scope of the present disclosure, various modules may be combined, or subsystem may be connect to other modules, various modifications and changes may be performed in the form and details of the disclosed methods and systems described above. For example, in some embodiments, the combined color table determination subunit 430 may be omitted or integrated into the retrieving subunit 420, and the retrieving subunit 420 directly output a retrieving result including one combined color table.

Figure 5:
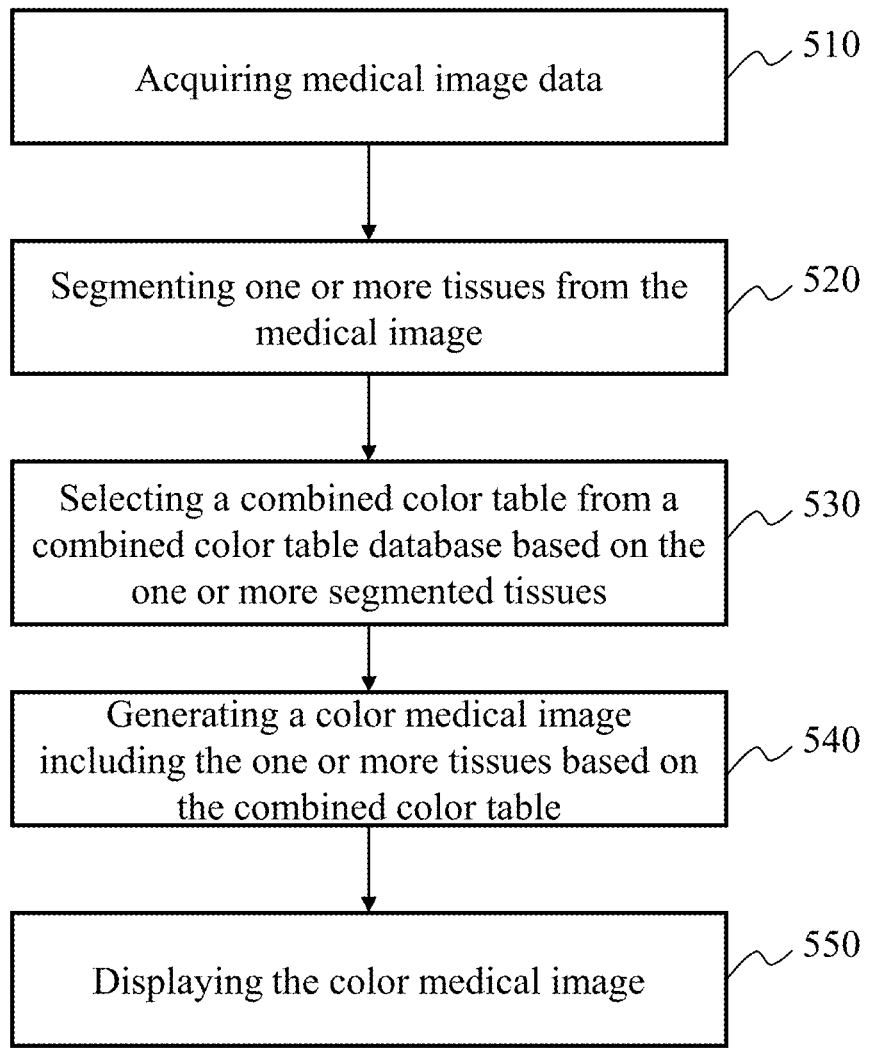
FIG. 5 is an exemplary flowchart of generating a color medical image according to some embodiments of the present disclosure.

FIG. 5 is an exemplary flowchart of generating a color medical image according to some embodiments of the present disclosure. The process of acquiring the color medical image may include: acquiring medical image data 510; segmenting one or more tissues in the image 520; determining the combined color table from a combined color table database based on the one or more segmented tissues 530; generating a color medical image including the one or more tissues based on the combined color table 540; and displaying the color medical image 550.

In 510, the medical image may be acquired. In some embodiments, the medical image may be acquired by the receiving module 310. The medical image may include grayscale images, such as an XR image, a CT image, an MR image, an ultrasound image, or any combination thereof. In some embodiments, the medical image may be acquired from the storage module 330. In some embodiments, the image data may be acquired from external data sources via the network 180. In some embodiments, the image data may be acquired from the input/output component 260. The related medical image acquisition method may refer to the description of the receiving module 310.

In 520, different tissues or different portions of a tissue in the medical image may be segmented. In some embodiments, the tissue segmentation may be implemented by the tissue segmentation unit 321. In some embodiments, the tissue segmentation may be based on one or more algorithms, for example, an image segmentation method based on the edge, such as a Perwitt operator method, a Sobel operator method, a gradient operator method, a Kirch operator method, and the like, an image segmentation method based on the region, such as a region growing method, a threshold method, a clustering procedure, and the like, the other segmentation methods, such as methods based on the fuzzy set or neural network, and the like, or any combination thereof. In some embodiments, the tissue segmentation may be based on Mesh structure, a Mask manner, or any combination thereof. The related tissue segmentation method may reference the description of the tissue segmentation unit 321.

In 530, the combined color table may be determined from a combined color table database based on the one or more segmented tissues. In some embodiments, the determination may be implemented by the combined color table selection unit 322. The determination may be based on the types of the tissues, or the different portions of a certain tissue. The determination may include: firstly, retrieving from the combined color table database based on the segmented tissues, and then determining one result from the retrieving results. The related combined color table determination method may refer to the description of the combined color table selection unit 322.

In 540, a color medical image may be generated based on the combined color table determined in 530. In some embodiments, the color medical image may be generated by the image generation unit 323. The related generation method may refer to the description of the image generation unit 323.

In 550, the color medical image generated in 540 may be displayed. In some embodiments, the output module 340 may transmit the color medical image to the interactive device 140 to display. The color medical image may be displayed to a user in a form of an image, audio or video.

It should be noted that the description of the process of generating the color medical image is only a specific example, and are not to be taken as the only possible implementation. It would be apparent to those skilled in the art that after knowing this basic principle of generating the images, various modifications and changes in the form and details of the embodiments and steps of generating the images may be implemented, and simple deductions or replacements may be implemented without departing from this basic principle, and the order of individual steps may be adjusted or combined without creative efforts, but the modifications and changes are still within the scope of the above description. In some embodiments, the steps 540 and 550 may be combined into one step. In some embodiments, after 540, the image data processing may return to 530 to further process the image data. For example, the combined color table may be re-determined and generated. In some embodiments, one or more operation may be added or deleted from the process. For example, before 510, a scan to the examined object may be added. The scan may be performed by the imaging device. For another example, a data storage operation may be added in between or after 510, 520, 530, 540 and/or 550. The data may be stored in the storage module 330.

Figure 6:
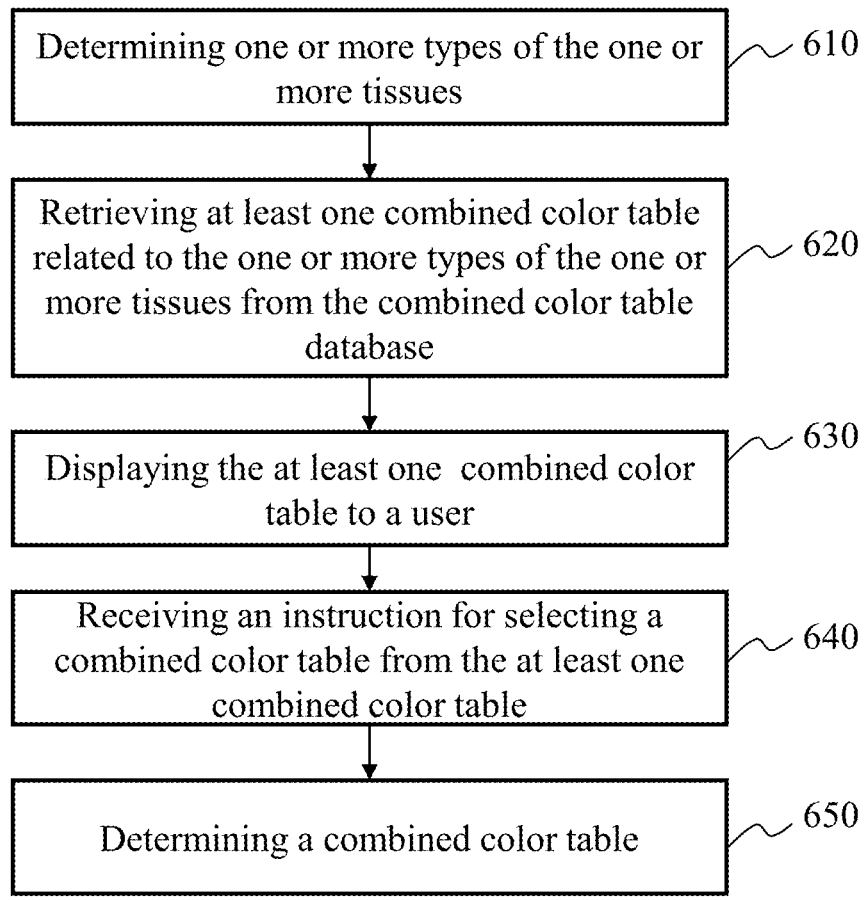
FIG. 6 is an exemplary flowchart of determining the combined color table from a combined color table database according to some embodiments of the present disclosure.

FIG. 6 is an exemplary flowchart of determining the combined color table from a combined color table database according to some embodiments of the present disclosure. The process of determining the combined color table from the combined color table may include: determining one or more types of the one or more tissues 610, retrieving related combined color tables based on the types of the tissues 620, displaying the related combined color table to a user 630, receiving an instruction for determining the combined color table 640, and determining the combined color table 650.

In 610, one or more types of the one or more tissues in received medical image may be determined. In some embodiments, the types of the tissues may be determined by the tissue type determination subunit 410. The determining types of the tissues include determining type features of the tissues. The type features include types of the tissues, amount of different tissues and morphology of the tissues. The related method for determining the types of the tissues may refer to the description of the tissue type determination subunit 410.

In 620, the at least one combined color tables may be retrieved based on the types of the tissues one or more tissues from the combined color table database. In some embodiments, the related combined color tables may be retrieved by the retrieving subunit 420. The retrieval may be performed based on the type features of the tissue determined in 610. The retrieval step may be performed hierarchically, and the range of the retrieving result may be reduced gradually. The related retrieval method may refer to the description of the retrieving subunit 420.

In 630, the at least one combined color table may be displayed to the user. In some embodiments, the combined color table may be displayed by the output module 340. The related combined color table may be the retrieving result in 620. In some embodiments, the retrieving results may be displayed in the interactive device 140. The displaying format may include a list, a schematic, and a preview image applying the combined color table to generate the color medical image. For example, a set of preview images applying different combined color tables may be displayed on a display device. The user may visually see the generating effect of the different combined color tables.

In 640, an instruction for selecting a combined color table from the at least one combined color table may be received. In some embodiments, the instruction may be received by the receiving module 310. The user may send an instruction for determining the combined color table by the interactive device 140. In some embodiments, the instruction for determining the combined color table may be an instruction of the retrieving results presented in 630. For example, a set of preview images applying different combined color tables are displayed on the display device. One preview image may be clicked and selected by a mouse, and this means that the instruction for determining the combined color table is sent.

In 650, a combined color table may be determined. In some embodiments, the combined color table may be determined by the combined color table determination subunit 430. The combined color table may be determined according to a user instruction acquired in 640. The determined combined color table may be a basis of generating the color medical image.

Figure 7:
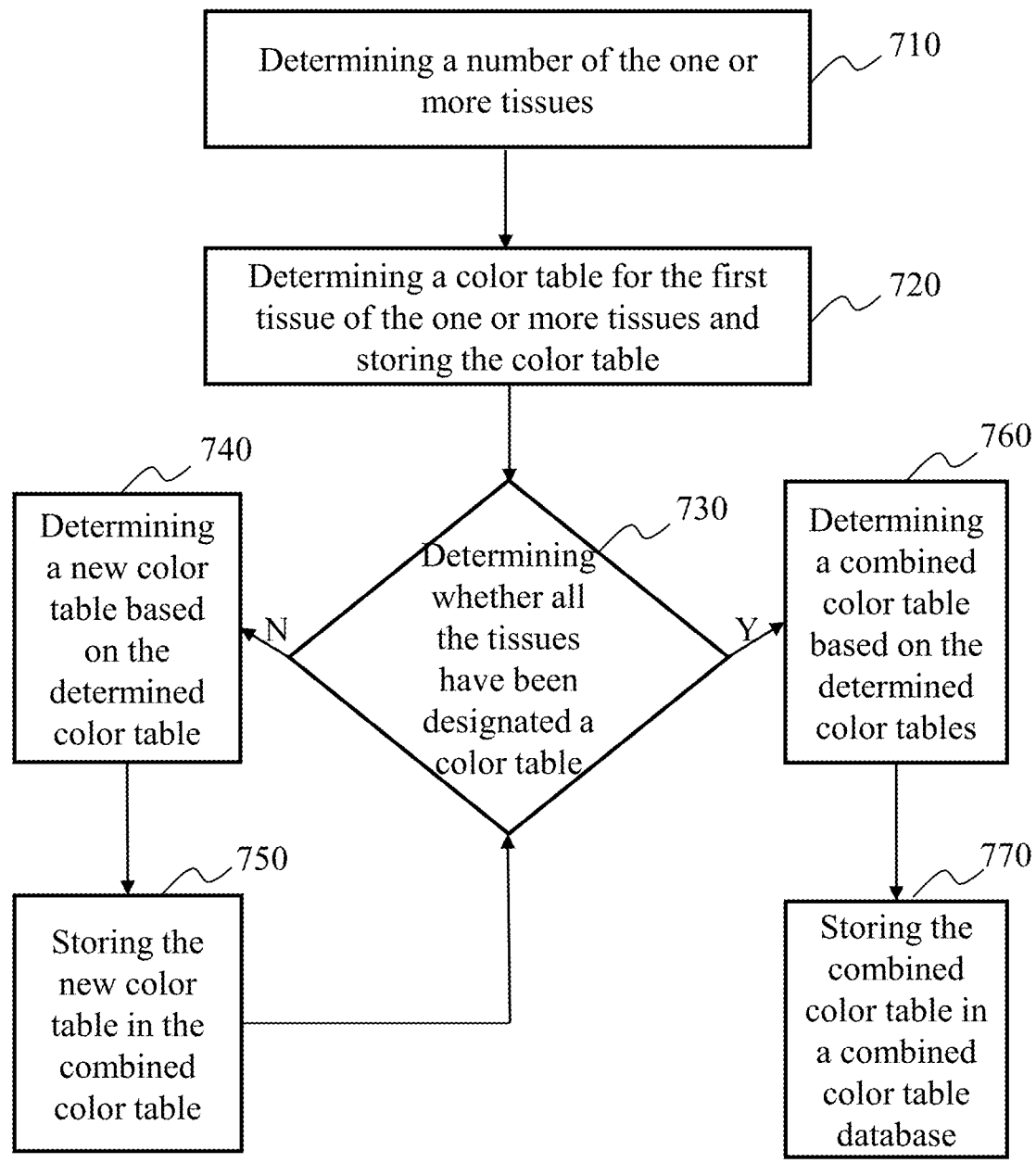
FIG. 7 is an exemplary flowchart of generating the combined color table database according to some embodiments of the present disclosure.

FIG. 7 is an exemplary flowchart of generating the combined color table database according to some embodiments of the present disclosure. The process of generating the combined color table database may include: determining a number of the tissues 710, determining a color table for the first tissue and storing the color table determining whether all the tissues have been designated a color table 730, determining a new color table based on the determined color table 740, storing the new color table in the combined color table 750, determining a combined color table based on the determined color table 760, and storing the combined color table in a combined color table database 770.

In 710, a number of the one or more tissues may be determined. During generating the combined color table database, a single combined color table may be first generated, and then a certain number of combined color tables constitute the combined color table database. The amount of the tissues in the combined color table may be first determined when the single combined color table may be generated. In some embodiments, the amount of the tissues may be the number of types of the tissues, or the amount of the different portions of a tissue (e.g., the amount of vertebras in vertebral images, and the like). In some embodiments, the amount of tissues may help generated a combined color table data unit. The data unit may be divided into several parts based on the number of the tissues. The several parts of the data unit may separately correspond to a certain kind of tissue or the different portions of a tissue. For example, the data unit of a certain combined color table may be divided into three parts, in which a first part represents information related to the bone, a second part represents information related to the left lung lobe, and a third part represents information related to the right lung lobe.

In 720, a color table may be determined for the first tissue of the one or more tissues and storing the color table. In some embodiments, the color table may be stored in the data unit in 710. The first tissue may be any one of the tissues or a specific kind of tissue determined in 710. For example, a kind of tissue may be selected arbitrarily as a first tissue needed to be determined, when the combined color table including the bone, the skin and the muscle is generated. In some embodiments, the priority of determining some tissue color tables is higher than the priority of determining the other tissue color tables, and the tissues may be considered as a first tissue. For example, when the bone, the skin and the muscle are displayed simultaneously, the high transparency of the skin is desired, and the skin may be taken as the first tissue to determine the color table thereof. The color table may include information about number, name, label, color, transparency, or whether to hide the tissues.

In 730, determining whether all the tissues have been designated a color table. If the color tables of some tissues have not determined, 740 may be performed. If the color tables of all tissues have been determined, 760 may be performed. In some embodiments, the above determination may be performed according to the judgment whether the amount of the color table data unit in 710 is the same as the number of the tissues. For example, the first tissue color table data is only one in the color table data unit when 730 is firstly performed. The current combined color table data unit is not filled with data, that is, the color tables of some tissues are not determined, and it continues to perform 740. For another example, if the number of tissues in the color table data unit corresponds to the number of tissues determined in 710, 760 may be performed.

In 740, a new color table may be determined based on the determined color table. In some embodiments, the information in the determined color table of the tissues may limit the information in the undetermined color table of the tissues. For example, if the color of the bone in the color table, that has been determined, is green, the color of the tissues in the color table, that will be determined later, cannot be green.

In 750, the new color table may be stored in the combined color table. The storing may be a storing by writing the information of the new determined color table to the combined color table data unit in 710. The writing may be a writing written into the data unit divided by the types of the tissues.

In 760, a combined color table may be determined according to the determined color table. In the judgment in 730, the color tables of all tissues have been determined, that is, all information in the combined color table data unit may already have been full. The information in the combined color table data unit may be determined as a combined color table.

In 770, the combined color table may be stored in the combined color table database. The storing may be performed by numbering the types of the determined tissues and storing the combined color table. The numbering may be performed by setting some labels for the combined color table, so that the combined color table may be retrieved based on a relationship between a retrieval word and the label when retrieving. For example, the label of the combined color table including the bone, the skin and the muscle may be set to a label including three kinds of the tissues, a label including the bone, a label including the skin, a label including the muscle, and the like.

Figure 8:
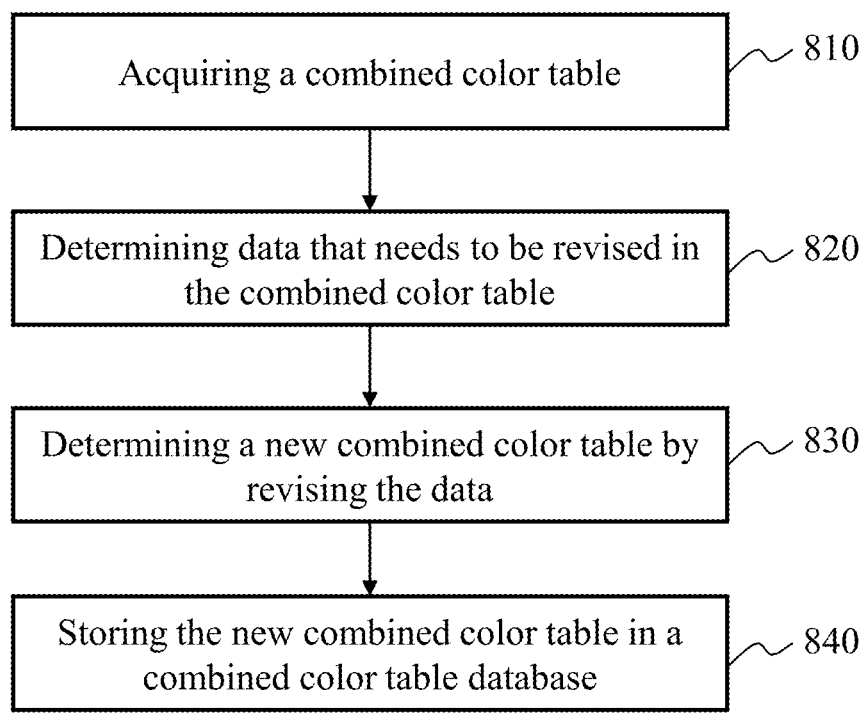
FIG. 8 is an exemplary flowchart of revising the combined color table according to some embodiments of the present disclosure.

FIG. 8 is an exemplary flowchart of revising the combined color table according to some embodiments of the present disclosure. The process of revising the combined color table may include: acquiring a combined color table 810, determining the data needs to be revised in the combined color table 820, determining a new combined color table by revising the data 830, and storing the new combined color table into the combined color table database.

In 810, a combined color table may be acquired. The combined color table may be invoked from the combined color table database, or be written by the user manually. In some embodiments, when the user applies a certain combined color table to assist with generating the color medical image, the effect may be poor, and needs to adjust some data. The user may write a combined color table manually according to the display effect. For example, the combined color table is filled with data corresponding to the current display effect according to a data structure of the combined color table data unit.

In 820, data needs to revised in the combined color table may be determined. In some embodiments, the effect of the color medical image, generated by the combined color table acquired in 810, may be poor, and the requirement of the user cannot be met. The users are likely to wish to revise some data in the combined color table. For example, since the color of the bone is closer to the color of the skin, it may be difficult to distinguish the two kinds of tissues. The data about the color of the bone or skin may be determined as data needing to be revised. As another example, the transparency of the skin is not high enough, which leads to a problem that inner tissue cannot be observed. The data about the transparency of the skin may be determined as data needing to be revised.

In 830, a new combined color table may be determined by revising the data. In some embodiments, the user may revise the data determined in 820 by revising corresponding data in the combined color table data unit. In some embodiments, a more user-friendly user interface may be used for displaying the data in the combined color table. For example, the data in the combined color table may correspond to various buttons on the display window, and the corresponding button may be clicked and selected to revise the data.

In 840, the new combined color table may be stored in a combined color table database. The storage method may refer to the description in 770. If the combined color table acquired in 810 is also from the same combined color table database, the data in the new combined color table may overwrite the data in existing combined color table.

Figure 9:
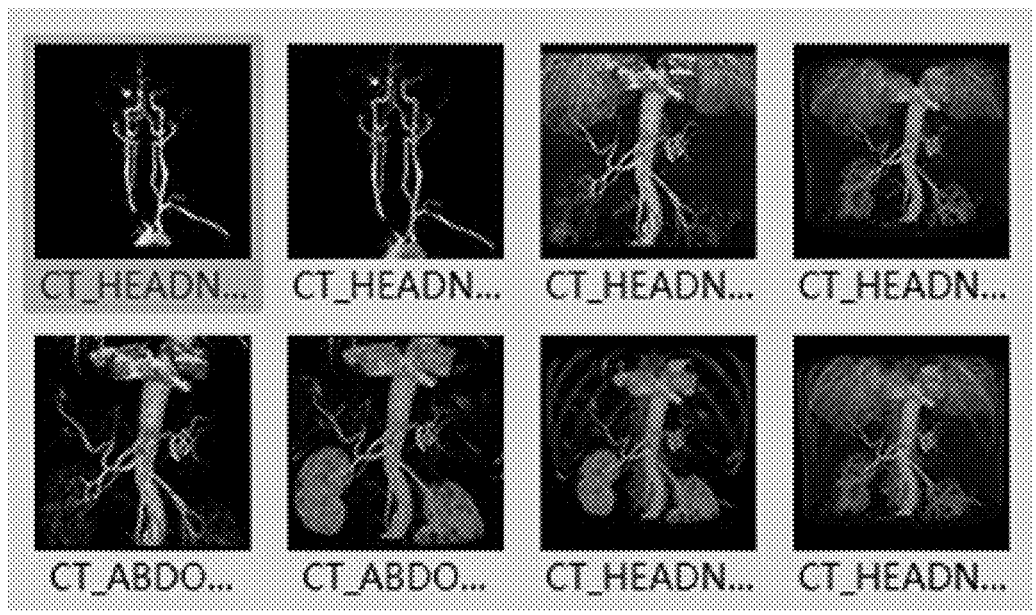
FIG. 9 is a diagram of determining the combined color table according to some embodiments of the present disclosure.
Figure 10A:
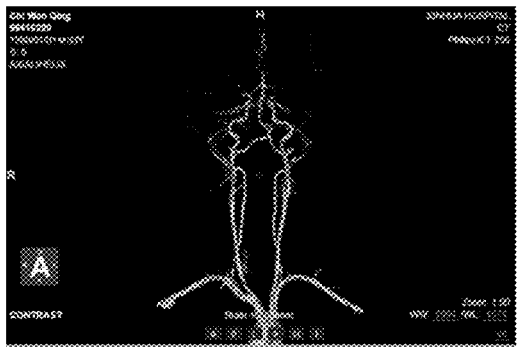
FIGS. 10A to 10D are diagrams of generating color medical image by the different combined color tables according to some embodiments of the present disclosure.
Figure 10B:
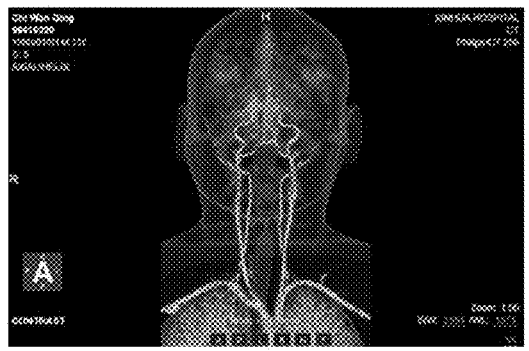
Figure 10C:
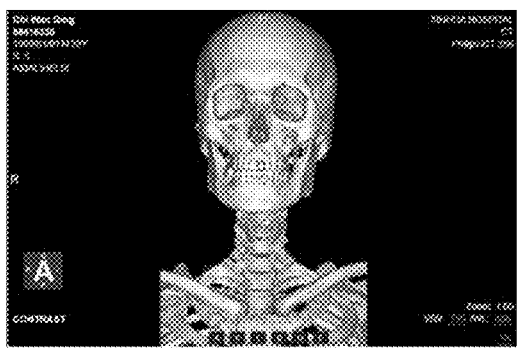
Figure 10D:

FIG. 9 is a diagram of determining the combined color table according to some embodiments of the present disclosure. Eight figures as shown in FIG. 9 may be preview images after the acquired medical image information applies the retrieving result of the combined color table. The user may visually see primary effect of the color medical image, which is generated according to different combined color table, on the screen, and one or more combined color tables may be selected by operation, such as click of the mouse, and the like.

FIGS. 10A to 10D are diagrams of generating color medical image by the different combined color tables according to some embodiments of the present disclosure. For the same medical image, different display effect may be obtained by applying the different combined color tables to generate the color medical image. The effect shown in FIG. 10A displays only head vessels, the effect shown in FIG. 10B displays the blood vessels and a skull, the effect shown in FIG. 10C displays the bone, and the effect shown in FIG. 10D displays the blood vessels, the skull and the skin.

Figure 11:
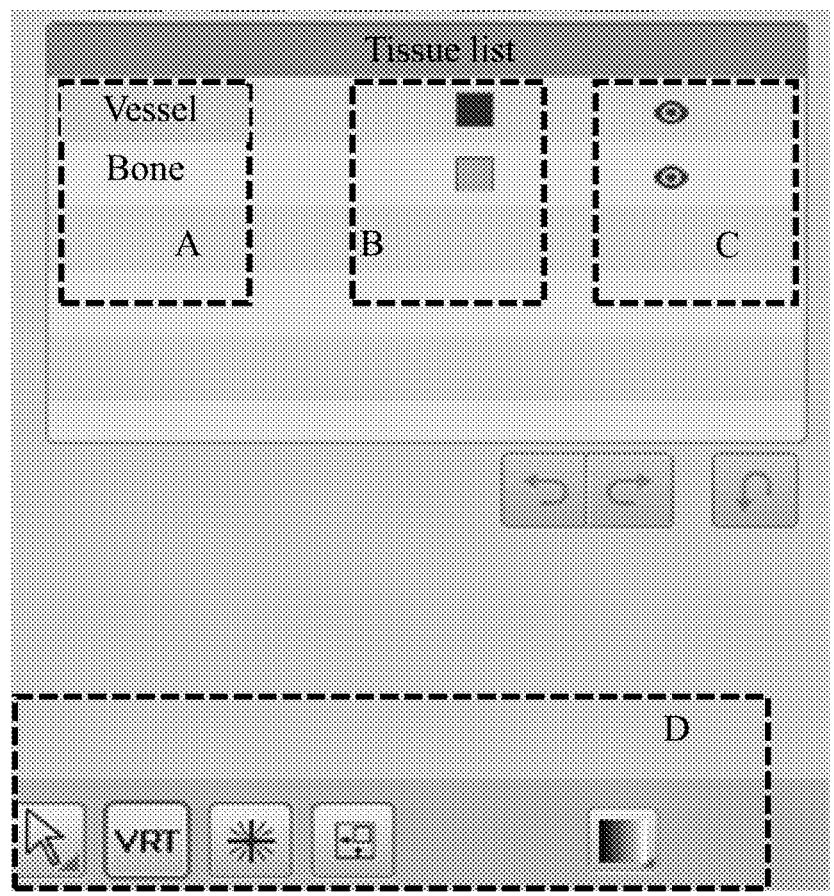
FIG. 11 is a diagram of revising a user interface of the combined color table according to some embodiments of the present disclosure.

FIG. 11 is a diagram of revising a user interface of the combined color table according to some embodiments of the present disclosure. The title of the user interface is a tissue list. The types of the tissues in the combined color table indicated by the dashed line box A are the blood vessel and the bone. The color adjusting information is indicated by the dashed line box B, and the user may adjust the color of the tissues by this button. The information for determining whether to hide the tissues is indicated by the dashed line box C, and the user may determine whether to hide the tissues by this button. The other data adjusting information is indicated by the dashed line box D, and the user may adjust the data, such as the transparency, the brightness, the contrast, and the like.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A method for generating color medical image comprising:
    acquiring medical image data;
    segmenting at least two tissues from the medical image data;
    determining a tissue number of the at least two tissues;
    determining a color table from a combined color table database for a first tissue of the at least two tissues;
    determining another color table from the combined color table database based on the determined color table for the first tissue of the at least two tissues until color tables for all of the at least two tissues are determined;
    combining the color tables for all of the at least two tissues as a combined color table; and
    generating a color medical image including the at least two tissues based on the combined color table,
    wherein the combined color table comprises data of color schemes for the segmented at least two tissues.

2. The method of claim 1, further comprising:
    displaying the color medical image including the at least two tissues to a user.

3. The method of claim 1, wherein the determining a combined color table from a combined color table database based on the at least two tissues comprises:
    determining at least one type of the at least two tissues;
    retrieving at least one combined color table related to the at least one type of the at least two tissues from the combined color table database;
    displaying the at least one combined color table to a user;
    receiving an instruction for selecting the combined color table from the at least one combined color table; and
    determining the combined color table.

4. The method of claim 1, further comprising a revising method for revising the combined color table in the combined color table database, the revising method comprising:
    acquiring the combined color table;
    determining data that needs to be revised in the combined color table;
    determining a new combined color table by revising the data; and
    storing the new combined color table in the combined color table database.

5. The method of claim 1, wherein the medical image data comprises at least one of a 2D image data, a 3D image data, and a dynamic image data.

6. The method of claim 1, wherein the segmenting at least two tissues from the medical image data comprises:
    segmenting different tissues from the medical image data; and
    segmenting different portions from a tissue of the at least two tissues.

7. The method of claim 1, wherein the color scheme comprises at least information of number, name, label, color, transparency, and whether to hide.

8. The method of claim 1, wherein the combined color table comprises:
    a subset of the medical image data corresponding to a plurality of tissues; and
    color tables corresponding to the plurality of tissue, respectively, each of the plurality of color tables comprising a window width and a window level with respect to the each of the plurality of tissues and a color effect corresponding to a gray value determined by the window width and window level.

9. The method of claim 3, wherein the determining at least one type of the at least two tissues comprises:
    determining at least one type feature of the at least two tissues, the at least one type feature of the at least two tissues comprising at least one type of the at least two tissues, a number of different types of the at least two tissues and morphology of the at least two tissues.

10. The method of claim 3, wherein the retrieving at least one combined color table related to the at least one type of the at least two tissues is based on at least one type feature of the at least two tissues.

11. The method of claim 1, wherein the combined color table further comprises one or more options as to whether to display or hide each of the at least two tissues.

12. A non-transitory computer readable medium storing executable instructions that, when executed by at least one processor, cause the at least one processor to effectuate a method comprising;
  acquiring medical image data;
  segmenting at least two tissues in the medical image data;
  determining a tissue number of the at least two tissues;
  determining a color table from a combined color table database for a first tissue of the at least two tissues;
  determining another color table from the combined color table database based on the determined color table for the first tissue of the at least two tissues until color tables for all of the at least two tissues are determined;
  combining the color tables for all of the at least two tissues as a combined color table; and
  generating a color medical image including the at least two tissues based on the combined color table,
  wherein the combined color table comprises data of color schemes for the segmented at least two tissues.

13. The non-transitory computer readable medium of claim 12, wherein the determining a combined color table from a combined color table database based on the at least two tissues comprises:
  determining at least one type of the at least two tissues;
  retrieving at least one combined color table related to the at least one type of the at least two tissues from the combined color table database;
  displaying the at least one combined color table to a user;
  receiving an instruction for selecting the combined color table from the at least one combined color table; and
  determining the combined color table.

14. A color image generating system comprising:
  at least one processor; and
  a storage medium storing executable instructions, when executed by at least one processor, cause the at least one processor to implement a method comprising:
  acquiring medical image data;
  segmenting at least two tissues from the medical image data;
  determining a tissue number of the at least two tissues;
  determining a color table from a combined color table database for a first tissue of the at least two tissues;
  determining another color table from the combined color table database based on the determined color table for the first tissue of the at least two tissues until color tables for all of the at least two tissues are determined;
  combining the color tables for all of the at least two tissues as a combined color table; and
  generating a color medical image including the at least two tissues based on the combined color table,
  wherein the combined color table comprises data of color schemes for the segmented at least two tissues.

15. The system of claim 14, wherein the determining a combined color table from a combined color table database based on the at least two tissues comprises:
  determining at least one type of the at least two tissues;
  retrieving at least one combined color table related to the at least one type of the at least two tissues from the combined color table database;
  displaying the at least one combined color tables to a user;
  receiving an instruction for selecting a combined color table from the at least one combined color table; and
  determining the combined color table.

16. The system of claim 15, wherein an instruction of determining the combined color table from the at least one combined color table is transmitted by a user via an interactive device, wherein
  the interactive device displays the at least one combined color table in a displaying format comprising list, diagram, and previews image generated by applying the combined color table to the medical image including the at least two tissues.

17. The system of claim 14, wherein the medical image data comprises at least one of a 2D image data, a 3D image data, and a dynamic image data.

18. The system of claim 14, wherein the segmenting at least two tissues from the medical image data comprises:
  segmenting different tissues from the medical image data; and
  segmenting different portions from a tissue of the at least two tissues.

19. The system of claim 14, wherein the combined color table comprises:
  a subset of the medical image data corresponding to a plurality of tissues; and
  color tables corresponding to the plurality of tissue, respectively, each of the plurality of color tables comprising a window width and a window level with respect to the each of the plurality of tissues and a color effect corresponding to a gray value determined by the window width and window level.

* * * * *